United States Patent
Zhang et al.

(10) Patent No.: US 12,318,757 B2
(45) Date of Patent: Jun. 3, 2025

(54) COMPOSITE MATERIALS FOR BIOSEPARATIONS

(71) Applicant: CHIRAL TECHNOLOGIES EUROPE SAS, Illkirch (FR)

(72) Inventors: Tong Zhang, Illkirch (FR); Pilar Franco, Illkirch (FR); Yasuto Morishita, Illkirch (FR); Klaus Gottschall, Heddesheim (DE)

(73) Assignee: CHIRAL TECHNOLOGIES EUROPE SAS, Illkirch (FR)

( * ) Notice: Subject to any disclaimer, the term of this patent is extended or adjusted under 35 U.S.C. 154(b) by 1126 days.

(21) Appl. No.: 16/978,475

(22) PCT Filed: Mar. 5, 2019

(86) PCT No.: PCT/EP2019/055383
§ 371 (c)(1),
(2) Date: Sep. 4, 2020

(87) PCT Pub. No.: WO2019/170634
PCT Pub. Date: Sep. 12, 2019

(65) Prior Publication Data
US 2021/0106974 A1    Apr. 15, 2021

(30) Foreign Application Priority Data
Mar. 5, 2018 (EP) .................... 18160024

(51) Int. Cl.
| | | |
|---|---|---|
| *B01J 20/26* | (2006.01) | |
| *B01D 15/20* | (2006.01) | |
| *B01D 15/34* | (2006.01) | |
| *B01D 15/38* | (2006.01) | |
| *B01J 20/28* | (2006.01) | |
| *B01J 20/285* | (2006.01) | |
| *B01J 20/32* | (2006.01) | |
| *B01J 20/34* | (2006.01) | |
| *C07K 1/22* | (2006.01) | |

(52) U.S. Cl.
CPC .......... *B01J 20/267* (2013.01); *B01D 15/203* (2013.01); *B01D 15/34* (2013.01); *B01D 15/3809* (2013.01); *B01J 20/28007* (2013.01); *B01J 20/285* (2013.01); *B01J 20/3204* (2013.01); *B01J 20/3282* (2013.01); *B01J 20/3425* (2013.01); *B01J 20/3475* (2013.01); *C07K 1/22* (2013.01)

(58) Field of Classification Search
CPC  B01J 20/3204; B01J 20/3475; B01J 20/3425; B01J 20/267; B01J 20/28007; B01J 20/285; B01J 20/3282; B01D 15/34; B01D 15/203; B01D 15/3809; C07K 1/22; C07K 1/34

See application file for complete search history.

(56) References Cited

U.S. PATENT DOCUMENTS

| | | |
|---|---|---|
| 4,339,500 A | 7/1982 | Yanagihara et al. |
| 5,372,820 A | 12/1994 | Dorgebray et al. |
| 2015/0298097 A1 | 10/2015 | Rahane et al. |
| 2017/0327534 A1 | 11/2017 | Rodrigo et al. |

FOREIGN PATENT DOCUMENTS

| | | |
|---|---|---|
| CN | 101039744 A | 9/2007 |
| CN | 101048222 A | 10/2007 |
| EP | 2 027 921 A2 | 2/2009 |
| EP | 2 545 989 A1 | 1/2013 |
| JP | 2-90943 A | 3/1990 |
| JP | 2004-331776 A | 11/2004 |
| JP | 2014-521078 A | 8/2014 |
| JP | 2016-6410 A | 1/2016 |
| JP | 2017-515099 A | 6/2017 |
| JP | 2017-122643 A | 7/2017 |
| WO | WO 95/25574 A1 | 9/1995 |
| WO | WO 2005/120701 A1 | 12/2005 |
| WO | WO 2006/015495 A1 | 2/2006 |
| WO | WO 2006/034575 A1 | 4/2006 |
| WO | WO 2011/140406 A1 | 11/2011 |

*Primary Examiner* — Shafiqul Haq
(74) *Attorney, Agent, or Firm* — Birch, Stewart, Kolasch & Birch, LLP

(57) ABSTRACT

The present invention relates to composite materials useful for purifying proteins obtained from biological feedstocks. The composite materials of the invention comprise a porous support having an average pore size of 5 to 500 nm, said porous support being filled with a first polymer which is cross-linked, and a second polymer which is not crosslinked and is covalently bonded to the external surface of the cross-linked polymer-filled porous support.

9 Claims, No Drawings

COMPOSITE MATERIALS FOR BIOSEPARATIONS

TECHNICAL FIELD

The present invention relates to composite materials useful for purifying proteins obtained from biological feedstocks.

BACKGROUND OF THE INVENTION

The relevance of proteins for use as bio-pharmaceuticals has continuously increased during the last decades in many therapeutic and diagnostic applications. One area of particular interest is the use of recombinant monoclonal antibodies (mAbs). The number of approved therapeutic mAbs and fragments thereof for the treatment of inflammatory diseases, diabetes, various cancers and blood disorders increases each year.

Due to the pharmacokinetic properties of mAbs, in many cases initial single doses in the range of about 0.1-1 g per patient are required, followed by a weekly or monthly administration of similar doses. Therefore, large amounts of therapeutic mAbs are needed and thus therapeutic mAbs must be manufactured on an industrial scale. The mAbs are manufactured in biological feedstocks such as fermentation broths (filtrates) and cell cultures which vary in the expression levels of secreted recombinant antibodies and in their impurities content.

To qualify as pharmaceuticals, target proteins must be essentially free of any product- or process-related impurities which are always found in cell culture supernatants or filtrates after harvesting (e.g., cells and cell debris from the secreted target proteins in the culture medium). These contaminants comprise not only proteins and nucleic acids (DNA and RNA) from genetically engineered host, e.g., Chinese Hamster Ovary-Host Cell Proteins (CHO-HCPs) and respective DNA (CHO-DNA), but also remaining cell culture supplements, including proteins added as nutrients or stabilizers (e.g., Bovine Serum Albumin—BSA or transferrin), salts, buffers, as well as endotoxins and pathogenic germs or fragments thereof.

The known methods for the purification of target proteins include the removal of viruses, endotoxins and to a certain extent nucleic acids by appropriate membrane filtration steps (e.g., by binding to strong anion exchanger membranes) and the removal of low molecular weight water-soluble contaminants during subsequent unit operations in Downstream Processing (DSP). The complete removal of the broad spectrum of different HCPs is, however, a difficult task, which so far has mainly been solved by the application of multiple dedicated preparative chromatography steps.

The chromatographic purification methods used in the DSP of mAbs and other recombinant protein products include affinity chromatography, cation and anion exchange, hydrophobic interaction, and metal chelate affinity. More recently a variety of multimodal and pseudo-affinity chromatography media became available and found their use in respective production processes, e.g., for product polishing after ion exchange or affinity chromatography steps (EP-A-1807205). In the currently applied chromatographic methods, two classical chromatographic modes are normally found: one based in continuous elution chromatographic processes and the other based on "bind-and-elute" concepts.

The common principle of these chromatographic separation methods is the selective adsorption capabilities of the various chromatography media towards one or more components from the biological samples. Thus, unbound (or weakly bound) components are separated from the (more) strongly bound ones and appear in the corresponding breakthrough fraction. Moreover, bound components can often be separated from each other by adjusting elution conditions to form a continuous or step gradient with increasing or decreasing ionic strength, pH or specific displacer concentration, in order to obtain a volume- and time-based change in conditions leading to selective desorption of individual components.

Among the available chromatographic methods, Size Exclusion Chromatography (SEC) is not considered useful for large scale operations, except for polishing purposes, due to its low productivity, low resolution and low speed. In contrast, one of the most broadly used first steps in the industrial chromatographic mAb purification platforms is based on a "capture" or "bind-and-elute" affinity mechanism. Such process involves the binding of the target compound ("capture"), whereas the majority of the undesired products are left unbound or may be separated from the target by a selective elution step, releasing bound impurities before or after the target substance. A representative example of such bind-and-elute process is the use of Protein A.

In affinity purification of mAbs, immunoglobulins are specifically bound to immobilized Protein A, under conditions favoring very strong binding of the target protein to the chromatographic material, while HCPs and other impurities remain largely unbound. Thus, after washing out the unbound components, the bound immunoglobulins can be released by changing the pH in the respective column from around neutral to rather acidic conditions (e.g., to pH 3) by flushing the column with an appropriate acidic buffer solution. In theory, the collected immunoglobulin product should be entirely pure after this step, due to the extraordinary high and specific selectivity of Protein A for binding to distinct genetically conserved structural motives of the antibody molecules. However, in real technical production processes a number of side effects prevent such perfect one step purification. Among these co-elution of residual HCPs, either bound to Protein A, the chromatography matrix material, or even to immunoglobulins, is observed. Furthermore, leaking of traces of Protein A and degradation products thereof may occur, showing potential to bind to the target proteins again, particularly after the necessary rapid adjustment of the pH back to a range compatible with antibody stability. Exposure of immunoglobulins to the specific process conditions of Protein A chromatography may also favor more or less irreversible product losses, due to intrinsic protein instability, e.g., aggregate formation, partial degradation by proteolysis and other adverse effects.

Thus, additional purification steps are always required, in order to achieve the high purity levels defined for pharmaceutical grade antibody products. These steps, including ion exchange and various multimodal chromatography methods, are necessary to further reduce HCPs and nucleic acid levels, as well as to remove protein aggregates and lower molecular mass antibody degradation products. Such purification steps contribute to further reduction in product yield and add costly operational and time consuming efforts to the overall production process. Thus, there is a need for technologies which can remove the majority of the impurities in a one step process.

A number of methods for the purification of mAbs and other proteins using composite adsorbents are known. In these methods, the composite adsorbents are typically packed into chromatographic columns.

WO95/025574 discloses a method for removing contaminants from a biological fluid comprising bringing said biological fluid into contact with a cross-linked hydrophobic polymeric network overlaying, but not covalently bound to, a porous mineral oxide matrix, having its interior porous volume substantially filled by said hydrophobic network, whereby hydrophobic and amphiphilic molecules with an average molecular mass below 10,000 Da are removed.

U.S. Pat. No. 6,783,962 B1 relates to a particulate material useful for the isolation/purification of bio-macromolecules. The particulate material has a density of at least 2.5 g/ml, the particles of the particulate material have an average diameter of 5-75 μm, and the particles of the particulate material are essentially constructed of a polymeric base matrix and a non-porous core material, said core material having a density of at least 3.0 g/ml. The polymeric base matrix includes pendant groups which are positively charged at pH 4.0 or which are affinity ligands for a bio-molecule.

WO2004/073843 discloses a composite material that comprises a support member that has a plurality of pores and a macroporous cross-linked gel filling the pores of the support member. Also disclosed is a process for adsorbing a biological molecule or a biological ion from a liquid, which comprises passing a liquid containing the biological molecule or biological ion through a composite material which bears binding sites that display specific interactions for the biomolecule on the macroporous gel.

EP-A-2545989 discloses a composite material for chromatographic applications which comprises a porous support and a cross-linked polymer on the surface of the porous support, wherein the ratio between the pore size [nm] of the porous support and the cross-linking degree [%] of the cross-linked polymer is from 0.25 to 20 [nm/%], and wherein the cross-linking degree is from 5 to 20% based on the total number of cross-linkable groups in the cross-linked polymer.

WO 2018/050849 discloses the preparation of a composite material comprising porous silica gel with a pore size of 25 nm and a cross-linked poly(vinylformamide-co-polyvinylamine).

WO 2006/015495 relates to a composite material comprising a porous support member durably filled or coated with a non-cross-linked polymer. The pore size of the porous support can be within the range of 0.1 to 5 μm. The composite material can be used for protein adsorption. This reference does not mention or suggest covalently bonding a non-cross-linked polymer to the external surface of the polymer-filled porous support.

WO 2005/120701 discloses a composite material comprising: a support member that has a plurality of pores extending therethrough, and a macroporous crosslinked gel that is located in, and fills, the pores of the support member, in which crosslinked gel is entrapped a stabilising polymer that is substantially water-insoluble but water swellable.

EP-A-2027921 describes a porous sorptive media comprising a substrate having a first external side and a second external side, both sides being porous, and a porous thickness between them, said substrate having a sorptive material substantially covering the solid matrix of the substrate and said first and second external surfaces, said sorptive material comprising a crosslinked polymer having attached primary amine groups.

WO 2011/140406 discloses a porous sorptive media comprising mixed cellulose esters supported on a non-woven substrate and coated with a crosslinked polymer having attached primary amine groups.

The present invention has been designed to overcome the limitations of existing technologies in the purification of bio-molecules.

SUMMARY OF THE INVENTION

The object of the present invention is to provide composite materials which achieve improved purification of proteins such as mAbs from biological feedstocks containing same.

The object of the present invention is achieved by a composite material according to appended claim 1.

Specifically, the present invention provides a composite material comprising:
 a porous support having an average pore size of 5 to 500 nm, said porous support being filled with a first polymer which is cross-linked, and
 a second polymer which is not crosslinked and is covalently bonded to the external surface of the cross-linked polymer-filled porous support.

The present invention is based on the surprising finding that the presence of a second polymer which is not cross-linked significantly improves the purification capability of the composite material compared to composite materials composed only of a porous support filled with a cross-linked polymer.

The present invention provides a composite material for purification of target proteins, from undesired compounds contained in the same solution or suspension. The composites are particularly suited for the efficient removal of impurities from manufactured biotherapeutics, such as mAbs, and could easily be integrated in clarification or downstream purification processes (DSP).

The composite material of the present invention can preferably simultaneously deplete DNA and HCPs from the protein-containing solutions obtained during protein production and can also achieve excellent protein recovery.

The invention is also directed to a method for producing the composite material comprising the steps of:
 a) soaking a porous support having an average pore size of 5 to 500 nm with a solution or a dispersion containing a first polymer, a cross-linker, and a solvent;
 b) cross-linking the first polymer with the cross-linker at a temperature below 250° C., and
 c) covalently bonding a second polymer to the external surface of the composite material obtained in step b).

Also, provided is the use of the composite material of the invention for purifying a target protein in a feedstock.

Further, the invention provides a method for purifying a target protein in a feedstock, said method comprising the steps of:
 i) contacting the feedstock with a composite material of the invention for a sufficient time;
 ii) separating the composite material from the purified feedstock;
 iii) optionally, isolating the purified target protein from the feedstock; and
 iv) optionally, washing the composite material with a solvent and collecting the obtained solution for further processing.

DETAILED DESCRIPTION

Composite Material

In the present specification, the terms "composite", "composite material" and "adsorbent" are used interchangeably.

In the present specification, any reference to a "pore size" means "average pore size".

The porous support material has an average pore size of 5 nm to 500 nm. In combination with any of the above or below embodiments, the average pore size is preferably 15 nm to 300 nm, more preferably 20 nm to 200 nm, further preferably 25 nm to 250 nm, even more preferably 30 nm to 200 nm, and most preferably 40 nm to 100 nm such as 50 nm to 100 nm. In the present specification, the average pore size of the porous support material is determined by mercury intrusion according to DIN 66133.

The porous support material can be a membrane, a hollow-fiber, a non-woven tissue, a monolithic or a particulate material. Particulate and monolithic porous materials are preferred. In a preferred embodiment in combination with any of the above or below embodiments, the porous support material is a particulate porous support material which has irregular or spherical shape.

In a further preferred embodiment, in combination with any of the above or below embodiments, the porous support material is composed of a metal oxide, a semi-metal oxide, a ceramic material, a zeolite, or a natural or synthetic polymeric material.

In a further preferred embodiment, in combination with any of the above or below embodiments, the porous support material is porous silica, alumina or titania particles.

In a further preferred embodiment, in combination with any of the above or below embodiments, the porous support material is porous silica gel.

In a further preferred embodiment, in combination with any of the above or below embodiments, the porous support material is a porous polysaccharide, such as cellulose, chitosan or agarose.

In a further preferred embodiment, in combination with any of the above or below embodiments, the porous support material is a porous synthetic polymer, such as polyacrylate, polymethacrylate, polyetherketone, polyalkymether, polyarylether, polyvinylalcohol, or polystyrene, or mixtures or copolymers thereof.

In a further preferred embodiment, in combination with any of the above or below embodiments, the porous support material is a particulate material with an average particle size (diameter) of 1 μm and 500 μm, preferably between 20 μm and 200 μm, more preferably 30 to 150 μm and most preferably 35 to 100 μm.

In the present specification, the average particle size (diameter) and the particle size distribution of the porous support is determined by Malvern Laser Diffraction.

In the present specification, unless otherwise specified, the term "first polymer" refers to the polymer before being cross-linked.

The first polymer (i.e. before being cross-linked) is not limited in any way, but preferably contains functional groups selected from hydroxyl (—OH), thiol (—SH), carboxyl (—COOH), sulfonyl (—SO$_3$H), amino, or combinations thereof.

In a preferred embodiment, in combination with any of the above or below embodiments, the first polymer contains hydroxyl groups, more preferably the first polymer is poly(vinylalcohol), agarose, or cellulose.

In a preferred embodiment, in combination with any of the above or below embodiments, the first polymer contains carboxyl groups, more preferably the first polymer is poly(meth)acrylate.

In a preferred embodiment, in combination with any of the above or below embodiments, the first polymer contains amino groups, and preferably is a polyamine. In a further preferred embodiment, in combination with any of the above or below embodiments, the polyamine comprises primary and/or secondary amino groups.

In a preferred embodiment, in combination with any of the above or below embodiments, the first polymer is a polyamine selected from polyallylamine, polyvinylamine, polybutylamine, polylysine, and copolymers thereof.

In a preferred embodiment, in combination with any of the above or below embodiments, the first polymer is a polyvinylamine or a polyallylamine. The polyvinylamines and polyallylamines include linear or branched homopolymers of vinylamine or allylamine and copolymers of vinylamine or allylamine and amino- or amido-groups. In a further preferred embodiment, in combination with any of the above or below embodiments, the polyvinylamine is a linear or branched homopolymer of vinylamine or a copolymer of vinylamine and vinylformamide. Preferably, the copolymer of vinylamine and vinylformamide comprises 1% to 70% vinylformamide units, more preferably 2% to 40% vinylformamide units, most preferably 5% to 25% vinylformamide units, based on the total number of structural units of the polymer. In a further preferred embodiment, in combination with any of the above or below embodiments, the polyallyamine is a linear or branched homopolymer of allylamine or a copolymer of allylamine and allylformamide. Preferably, the copolymer of allylamine and allylformamide comprises 1% to 70% allylformamide units, more preferably 2% to 40% allylformamide units, most preferably 5% to 25% allylformamide units, based on the total number of structural units of the polymer.

In a preferred embodiment, in combination with any of the above or below embodiments, the first polymer has a weight average molecular weight (Mw) of 2,000 to 500,000 Da, preferably 10,000 to 450 Da, more preferably 15,000 to 400,000 Da, even more preferably 20,000 to 300,000 Da, and most preferably 25,000 to 250,000 Da.

In the present specification, the weight average molecular weight (Mw) of a polymer is determined by size exclusion chromatography (SEC) coupled to multi-angle-light scattering and refractive index detectors (SEC-MALS-RI).

In a preferred embodiment, in combination with any of the above or below embodiments, the first polymer is a polyvinylamine or polyallylamine having a hydrolysis degree of the formamide groups of at least 50%, preferably 60% to 99%, more preferably 66% to 94%, even more preferably 68% to 90%, and most preferably 70% to 86%.

In the present specification, the term "hydrolysis degree" refers to the "hydrolysis degree of the formamide groups of the polymer".

In a further preferred embodiment, in combination with any of the above or below embodiments, the first polymer is a polyvinylamine or polyallylamine having a weight average molecular weight (Mw) of 15,000 to 80,000 Da, preferably 20,000 to 70,000 Da, more preferably 25,000 to 50,000 Da and a hydrolysis degree of the formamide groups of 66% to 99%, preferably 67% to 90%, even more preferably 68% to 80%, and most preferably 68% to 75%.

In a further preferred embodiment, in combination with any of the above or below embodiments, the first polymer is a polyvinylamine or polyallylamine having a weight average molecular weight (Mw) of 100,000 to 500,000 Da, preferably 150,000 to 400,000 Da, more preferably 200,000 to 300,000 Da and a hydrolysis degree of 70% to 99%, preferably 75% to 95%, more preferably 75% to 90%.

In the present specification, the hydrolysis degree of the formamide groups of the polymer is determined by $^1$H-NMR according to the following method:

5.25 g of the polymer is weighted into a flask and 10 ml of water is added. The obtained mixture is rotated to get a homogenous composition and finally evaporated at 50° C. under vacuum until a dry solid is observed. The solid is dried under high vacuum (≤0.1 mbar) in an oven at 80° C. for 15 h to yield a dry residue.

The degree of hydrolysis is determined by $^1$H-NMR (400 MHz apparatus from Brucker, solvent: $D_2O$) based on the quantification of hydrolysed groups versus total hydrolysable groups according to the method described in reference:

Q. Wen, A. M. Vincelli, R. Pelton, "Cationic polyvinylamine binding to anionic microgels yields kinetically controlled structures", *J Colloid Interface Sci.* 369 (2012) 223-230.

In a further preferred embodiment, in combination with any of the above or below embodiments, the first polymer is cross-linked to a cross-linking degree of 5 to 25%. In a preferred embodiment, in combination with any of the above or below embodiments, the cross-linking degree is 6 to 15%, preferably 7 to 12%, more preferably 8 to 9%.

In the present specification, the "cross-linking degree" is defined as the cross-linker/polymer ratio (also referred to as "cross-linker ratio"). The "cross-linker ratio" is defined as the percentage in mol of the cross-linker versus the vinylamine structural units present in the polymer solution (based on average molecular weight) used for the reaction.

That is, the cross-linker ratio is calculated by the following formula (1):

$$\text{cross linker ratio} = \frac{V1 \times d1 \times C1 \times Mw2}{W2 \times C2 \times Mw1} \times 100\% \quad (1)$$

wherein V1 (ml) is the volume of cross-linker, d1 (g/ml) is the density of cross-linker, C1 (wt %) is the concentration of cross-linker, W2 (g) is the weight of polymer solution, C2 (wt %) is the concentration of polymer, Mw1 (g/mol) is the molecular weight of cross-linker and Mw2 (g/mol) is the average monomer unit molecular weight.

Mw2 is calculated by the following formula (2):

$$Mw2 = (\Sigma_k Nk \times Mk)/\Sigma_k Nk \quad (2)$$

wherein Nk is the number of monomer units of type k forming the polymer and Mk is the molecular weight (g/mol) of a monomer unit of type k.

The second polymer is not limited in any way but preferably contains functional groups selected from hydroxyl (—OH), thiol (—SH), carboxyl (—COOH), sulfonyl (—$SO_3H$), amino, or combinations thereof.

In a preferred embodiment, in combination with any of the above or below embodiments, the second polymer contains hydroxyl groups, more preferably the second polymer is poly(vinylalcohol), agarose, or cellulose.

In a preferred embodiment, in combination with any of the above or below embodiments, the second polymer contains carboxyl groups, more preferably the second polymer is poly(meth)acrylate.

In a preferred embodiment, in combination with any of the above or below embodiments, the second polymer contains amino groups, and preferably is a polyamine. In a further preferred embodiment, in combination with any of the above or below embodiments, the polyamine comprises primary and/or secondary amino groups.

In a preferred embodiment, in combination with any of the above or below embodiments, the second polymer is a polyamine selected from polyallylamine, polyvinylamine, polybutylamine, polylysine, and copolymers thereof.

In a preferred embodiment, in combination with any of the above or below embodiments, the second polymer is a polyvinylamine or a polyallylamine. The polyvinylamines and polyallylamines include linear or branched homopolymers of vinylamine or allylamine and copolymers of vinylamine or allylamine and amino- or amido-groups.

In a further preferred embodiment, in combination with any of the above or below embodiments, the polyvinylamine is a linear or branched homopolymer of vinylamine or a copolymer of vinylamine and vinylformamide. Preferably, the copolymer of vinylamine and vinylformamide comprises 1% to 70% vinylformamide units, more preferably 2% to 40% vinylformamide units, most preferably 5% to 25% vinylformamide units, based on the total number of structural units of the polymer.

In a further preferred embodiment, in combination with any of the above or below embodiments, the polyallylamine is a linear or branched homopolymer of allylamine or a copolymer of allylamine and allylformamide. Preferably, the copolymer of allylamine and allylformamide comprises 1% to 70% allylformamide units, more preferably 2% to 40% allylformamide units, most preferably 5% to 25% allylformamide units, based on the total number of structural units of the polymer.

In a preferred embodiment, in combination with any of the above or below embodiments, the second polymer has a weight average molecular weight (Mw) of at least 15,000 Da, preferably 20,000 to 1,000,000 Da, more preferably 25,000 to 500,000 Da, further preferably 30,000 to 300,000, even more preferably 50,000 to 300,000 Da, most preferably 80,000 to 250,000 Da.

In a preferred embodiment, in combination with any of the above or below embodiments, the second polymer is polyvinylamine or polyallylamine having a hydrolysis degree of the formamide groups of at least 50%, preferably 60% to 99%, more preferably 66% to 94%, even more preferably 68% to 90%, and most preferably 70% to 86%.

In a further preferred embodiment, in combination with any of the above or below embodiments, the second polymer is a polyvinylamine or polyallylamine having a weight average molecular weight (Mw) of 15,000 to 80,000, preferably 20,000 to 70,000, more preferably 25,000 to 50,000 and a hydrolysis degree of 66% to 99%, preferably 67% to 90%, even more preferably 68% to 80%, and most preferably 68% to 75%.

In a further preferred embodiment, in combination with any of the above or below embodiments, the second polymer has a weight average molecular weight (Mw) of 100,000 to 500,000, preferably 150,000 to 400,000, more preferably 200,000 to 300,000 and a hydrolysis degree of 70% to 99%, preferably 75% to 95%, more preferably 75% to 90%.

In a preferred embodiment, in combination with any of the above or below embodiments, the first polymer has the same weight average molecular weight (Mw) as the second polymer.

In a preferred embodiment, in combination with any of the above or below embodiments, the first polymer (i.e. before being cross-linked) is identical to the second polymer.

In another preferred embodiment, in combination with any of the above or below embodiments, the weight average molecular weight (Mw) of the second polymer is higher than the weight average molecular weight (Mw) of the first polymer.

In a further preferred embodiment, in combination with any of the above or below embodiments, the first polymer has a weight average molecular weight (Mw) of 10,000 to 100,000, preferably 15,000 to 50,000, more preferably 20,000 to 30,000, and the second polymer has a weight average molecular weight (Mw) of 100,000 to 500,000, preferably 150,000 to 300,000, more preferably 200,000 to 250,000.

In a preferred embodiment, in combination with any of the above or below embodiments, the total concentration of first polymer and second polymer is at least 3% w/w, preferably at least 5% w/w, more preferably, at least 7% w/w, and is preferably less than 25% w/w, more preferably less than 20% w/w, most preferably less than 15%, based on the total weight of the dry composite material.

The composite material of the present invention may comprise additional layers of non-crosslinked polymers, said non-crosslinked polymers being covalently bonded to the cross-linked polymer-filled porous support and/or to the second non-crosslinked polymer.

In a preferred embodiment, in combination with any of the above or below embodiments, the composite material comprises 1 to 3 additional layers of non-crosslinked polymers, which can be the same or different than the second polymer. Said additional layers of non-crosslinked polymers should be covalently bonded to each other and to the cross-linked polymer-filled porous support and/or to the second polymer.

In another preferred embodiment, in combination with any of the above or below embodiments, the composite material does not comprise additional layers of non-crosslinked polymers (i.e. the only polymers present in the composite material are the first polymer and the second polymer).

Method for Producing the Composite Material

The composite material of the present invention can be produced according to the following method:
    a) soaking a porous support having an average pore size of 5 to 500 nm with a solution or a dispersion containing a first polymer, a cross-linker, and a solvent;
    b) cross-linking the first polymer with the cross-linker at a temperature below 250° C., and
    c) covalently bonding a second polymer to the external surface of the composite material obtained in step b).

Any cross-linker having at least two reactive groups can be used in the present invention.

In a preferred embodiment, in combination with any of the above or below embodiments, the cross-linker is selected from bis-epoxides, dialdehydes, and diglycidylethers. In a more preferred embodiment, in combination with any of the above or below embodiments, the cross-linker is selected from propanediol diglycidylether, butanediol diglycidylether, hexanediol diglycidylether, polyethylene glycol diglycidyl ether, glutaric dialdehyde and succinic dialdehyde. More preferably, the cross-linker is selected from butanediol diglycidylether and hexanediol diglycidylether.

If the first polymer does not comprise cross-linkable groups, prior to step a) of the above method, the first polymer is functionalized with cross-linkable groups by any method known in the art.

In a preferred embodiment, in combination with any of the above or below embodiments, the cross-linker ratio is 6 to 15% (mol/mol), more preferably 7 to 12% (mol/mol), and most preferably 8 to 9% (mol/mol).

Any solvent or medium capable of dissolving or dispersing the polymer and the cross-linker may be used provided that it does not react or only slowly reacts with the cross-linker and the polymer under the conditions of step b) of the above method. Slowly, in this context, means that no observable reaction between the cross-linker and the solvent and between the polymer and the solvent occurs for the duration of step b).

In a preferred embodiment, in combination with any of the above or below embodiments, the solvent is a polar protic or a polar aprotic solvent. In a preferred embodiment, in combination with any of the above or below embodiments, the solvent is a polar protic solvent selected from water, $C_{1-6}$ alcohols (e.g. methanol, ethanol, isopropanol, and butanol) and mixtures thereof. Water is most preferred.

In a preferred embodiment, in combination with any of the above or below embodiments, the pH of the polymer-cross-linker solution employed in step a) is adjusted to 8 to 13, preferably 9 to 11, most preferably 10 to 11. The pH adjustment can be carried out by adding a strong base such as NaOH or KOH.

During step b) of the above method, the temperature is preferably between 20 to 180° C., more preferably 40 to 100° C., and most preferably 50° C. and 80° C.

In a preferred embodiment, in combination with any of the above or below embodiments, the duration of step b) is preferably between 1 hour and 100 hours, more preferably between 8 to 60 hours, and most preferably between 18 hours and 48 hours.

In a further preferred embodiment, in combination with any of the above or below embodiments, step b) is carried out at 40 to 100° C. for 8 to 60 hours, preferably at 50 to 80° C. for 12 to 50 hours, more preferably at 60° C. for 24 to 48 hours.

The covalent bonding of the second polymer to the external surface of the composite material obtained in step b) can be achieved by any means known in the art. The reaction which takes place on the external surface of the composite material obtained in step b) may comprise polymerizations or any grafting-from and any grafting-to techniques.

In a further preferred embodiment, in combination with any of the above or below embodiments, the second polymer is dissolved in a suitable solvent or medium. Any solvent capable of dissolving the second polymer may be used provided that it does not react or only slowly reacts with the polymer under the conditions of step c) of the above method. Slowly, in this context, means that no observable reaction between the second polymer and the solvent occurs for the duration of step c).

In a preferred embodiment, in combination with any of the above or below embodiments, the solvent for the second polymer is a polar protic or a polar aprotic solvent. In a preferred embodiment, in combination with any of the above or below embodiments, the solvent for the second polymer is a polar protic solvent selected from water, $C_{1-6}$ alcohols (e.g. methanol, ethanol, isopropanol, and butanol) and mixtures thereof. Water is most preferred.

In a preferred embodiment, in combination with any of the above or below embodiments, the pH of the second polymer-containing solution which can be employed in step c) is adjusted to 8 to 13, preferably 9 to 11, most preferably 10 to 11. The pH adjustment can be carried out by adding a strong base such as NaOH or KOH.

In a preferred embodiment, in combination with any of the above or below embodiments, the covalent bonding of the second polymer to the external surface of the composite material obtained in step b) is achieved via the cross-linker still present on the external surface of the composite material obtained in step b).

In the present specification, the term "non-crosslinked polymer" refers to a polymer which has not been subjected to active crosslinking through the addition of a crosslinker to the polymer. Thus, for the embodiment in which the second polymer is dissolved in a solvent, said solvent does not contain any cross-linkers.

In a further preferred embodiment, in combination with any of the above or below embodiments, the method further comprises a step d) of hydrolysing any unreacted cross-linkable groups of the cross-linker after step c).

Uses of the Composite Material

In the present specification, the terms "feedstock" and "feed" are used interchangeably.

In the present specification, term "proteins" includes polypeptides. Such polypeptides preferably contain at least 20 amino acid residues, more preferably between 40 and 80 amino acid residues.

The composite material of the present invention is useful for purifying a target protein in a feedstock.

In a preferred embodiment, in combination with any of the above or below embodiments, the feedstock comprises host cell proteins (HCPs), and DNA, and optionally RNA and other nucleic acids.

In the present invention, the feedstock optionally contains albumins, endotoxins, detergents and microorganisms, or fragments thereof.

The invention also provides a method for purifying a target protein in a feedstock, said method comprising the steps of:
i) contacting the feedstock with a composite material according to the invention for a sufficient time;
ii) separating the composite material from the purified feedstock;
iii) optionally, isolating the purified target protein from the feedstock; and
iv) optionally, washing the composite material with a solvent and collecting the obtained solution for further processing. In a preferred embodiment, in combination with any of the above or below embodiments, the target protein is a recombinant protein such as a monoclonal antibody (mAb) (e.g. Human immunoglobulin (hIgG)).

In a preferred embodiment, in combination with any of the above or below embodiments, the solvent of the feedstock is water optionally containing buffer(s), salt(s) and/or modifier(s).

In a preferred embodiment, in combination with any of the above or below embodiments, the feedstock is a fermentation broth supernatant (before or after filtration) or a cell culture supernatant (CCS) comprising the target protein and DNA, RNA, or other nucleic acids, and Host cell proteins (HCPs) as impurities.

In a preferred embodiment, in combination with any of the above or below embodiments, the composite material is used in a batch adsorption process. In this embodiment, in step i) of the purification method of the invention, the composite material is dispersed in the feedstock and in step ii), the composite material is separated from the feedstock (e.g. by centrifugation).

In another preferred embodiment, in combination with any of the above or below embodiments, the composite material is packed in a chromatography column.

In the method for recovering a target protein of the present invention, the feedstock is contacted with the composite material according to the invention for a sufficient time. In a preferred embodiment, in combination with any of the below embodiments, the contact time is 1 min to 10 hours, preferably 3 min to 5 hours, more preferably 5 min to 1 hour.

In a preferred embodiment, in combination with any of the above or below embodiments, prior to contacting the composite material with the feedstock, the composite material is equilibrated in an aqueous solution with a pH below 8, preferably 3 to 7.5, more preferably 4 to 7, and most preferably 5 to 6. The pH of the aqueous solution can be adjusted with any suitable buffer. For example, monobasic acids or salts thereof can be used for adjusting the pH. Preferred monobasic acids are formic, acetic, sulfamic, hydrochloric, perchloric acid, and glycine. Preferred salts of the monobasic acids are ammonium, alkyl ammonium, sodium and potassium salts.

In a preferred embodiment, in combination with any of the above or below embodiments, the pH is adjusted with ammonium acetate.

In a further preferred embodiment, in combination with any of the above or below embodiments, the pH is adjusted with phosphate-buffered saline (PBS).

In a preferred embodiment, in combination with any of the above or below embodiments, the ratio of feedstock to composite material (volume of feed to weight of dry composite material) is in the range of 2:1 to 100:1, preferably 5:1 to 80:1, more preferably 10:1 to 70:1, most preferably 20:1 to 50:1. High ratios of feedstock to composite material are preferred from the viewpoint of achieving efficient utilization of the composite material.

In a preferred embodiment, in combination with any of the above or below embodiments, the composite material separated in step ii) of the above method, which contains adsorbed impurities, is subjected to an elution procedure to elute said impurities, thereby regenerating the composite material for further use.

The method for purifying a target protein of the present invention may contain additional purification steps known in the art. Examples of such purification steps include ion exchange chromatography, addition of flocculation or precipitation agents, centrifugation, crystallization, affinity chromatography (e.g. employing separation media harboring Protein A, Protein G, or a combination thereof), membrane filtration, depth filtration (with diatomaceous earth or activated carbon) and application of a monolithic separation agent.

In a preferred embodiment, in combination with any of the above or below embodiments, steps i) and ii) of the method for separating a target protein of the invention are repeated in sequence multiple times (e.g. 2, 3, 4, 5, 6 times) using the same or different composite materials according to the present invention.

The following examples illustrate the invention.

EXAMPLES

Starting Materials Used in the Examples

The following starting materials have been used in the preparation of the composite materials of the examples:

Polymers:
  A1 Lupamin 4570 (supplied by BASF) (a co-polymer of vinylamine and vinylformamide)
  A2 Lupamin 4570 further hydrolyzed to 68% hydrolysis degree
  A3 Lupamin 4570 further hydrolyzed to 86% hydrolysis degree
  A4 Lupamin 4570 further hydrolyzed to 99% hydrolysis degree
  A5 Lupamin 9095 (supplied by BASF) (a co-polymer of vinylamine and vinylformamide)
  A6 Lupamin 9095 further hydrolyzed to 99% hydrolysis degree A7 Lupamin 4500 (supplied by BASF) (a co-polymer of vinylamine and vinylformamide)

A8 Lupamin 4500 further hydrolyzed to 23% hydrolysis degree

A9 Lupamin 9030 (supplied by BASF) (a co-polymer of vinylamine and vinylformamide)

A10 poly(allylamine hydrochloride) (supplied by Sigma-Aldrich)

Polymers A2 to A4, A6 and A8 were obtained by further hydrolysing polymers A1, A5, and A7 as follows.

Polymer A1, A5 or A7 was homogenized by gentle agitation for 30 min on a rotation station. A weighed amount of the homogenised polymer was placed in a round flask and a sodium hydrate solution in water was added and heated at 80° C. for several hours under the protection of $N_2$ stream. The mixture was subsequently cooled at room temperature (23° C.) and the pH adjusted by using a hydrochloric acid solution. The exact conditions are listed in Table 1.

TABLE 1

Experimental conditions for obtaining polymers A2 to A4, A6 and A8

| Polymer | Starting polymer | Hydrolysis degree | Amount (g) in reaction | Sodium hydrate solution | Conditions (Temp/time) | Conc. HCl solution | Final pH |
|---|---|---|---|---|---|---|---|
| A2 | A1 | 68% | 1150 | 300 g/10% | 80° C./5 h | 10% | 9.5 |
| A3 | A1 | 86% | 500 | 100 g/30% | 90° C./72 h | 25% | 9.5 |
| A4 | A1 | 99% | 500 | 100 g/48% | 90° C./24 h | 25% | 11-12 |
| A6 | A5 | 99% | 500 | 100 g/48% | 90° C./24 h | 25% | 11-12 |
| A8 | A7 | 23% | 200 | 28 g/25% | 70° C./2 h | 25% | 8 |

The properties of the polymers A1 to A10 are given in Table 2 below.

TABLE 2

Properties of the polymers A1 to A10

| Polymer | Polymer hydrolysis degree*[1] | Polymer concentration*[2] | dn/dc (ml/g) | Mw | Mw/Mn |
|---|---|---|---|---|---|
| A1 | 65% | 15% | 0.2997 | 29,600 | 1.8 |
| A2 | 68% | 11% | 0.3104 | 25,200 | 1.2 |
| A3 | 86% | 10% | 0.4219 | 25,200 | 1.3 |
| A4 | 99% | 7% | 0.4219 | 25,000 | 1.2 |
| A5 | 74% | 7% | 0.3842 | 205,000 | 1.3 |
| A6[3] | 99% | 4% | — | — | — |
| A7 | 5% | 8.0% | 0.6974 | 12,600 | 1.1 |
| A8 | 23% | 5.8% | 0.8192 | 11,500 | 1.3 |
| A9 | 35% | 9.6% | 0.2238 | 246,500 | 1.2 |
| A10 | N/A | 58% as free amine | 0.2284 | 23,300 | 2.9 |

*[1]The degree of hydrolysis was determined by $^1$H-NMR.
*[2]The concentration was estimated based on elemental analysis.
*[3]Fully hydrolysed Lupamin 9095 was not soluble in the media used to run the Mw determinations.

1) Hydrolysis Degree

The hydrolysis degree of the formamide groups of polymers A1 to A9 was determined by $^1$H-NMR as follows.

The polymer samples were prepared for NMR analysis with the following general protocol:

5.25 g of the commercial or further hydrolysed polymer was weighted into a flask and 10 ml of water were added. The mixture was rotated to get a homogenous composition and finally evaporated at 50° C. under vacuum until the dry solid was observed. The solid was dried under high vacuum (≤0.1 mbar) in an oven at 80° C. for 15 h to yield a dry residue.

The degree of hydrolysis was determined by $^1$H-NMR based on the quantification of free amine groups versus formamide groups according to the method described in reference:

Q. Wen, A. M. Vincelli, R. Pelton, "Cationic polyvinylamine binding to anionic microgels yields kinetically controlled structures", *J Colloid Interface Sci.* 369 (2012) 223-230.

The $^1$H-NMR system used for the measurements was a 400 MHz. The dry sample was dissolved in $D_2O$.

2) Polymer Concentration

The polymer concentration of polymers A1 to A10 was determined based on elemental analysis. The samples were prepared with the same protocol described in the $^1$H-NMR section until getting a dry residue. The elemental analyser was a FLASH 2000 Organic Elemental Analyzer (Thermo Scientific).

3) Weight-Average Molecular Weight (Mw), Polydispersity (Mw/Mn), and Specific Increment of Refractive Index (dn/dc) of the Polymers The weight-average molecular weight (Mw), polydispersity (Mw/Mn), and specific increment of refractive index (dn/dc) of the polymers are determined as follows.

Size exclusion chromatography (SEC) coupled to multi-angle-light scattering and refractive index detectors (SEC-MALS-RI) was used to determine the weight-average molecular weight (Mw) using the Rayleigh-Gans-Debye equation with Zimm formalism.

In this approach the light scattering signal is assumed to be proportional to average molecular weight and sample concentration at any point in a chromatogram, and specific increment of refractive index (dn/dc). Thus, light scattering detectors coupled with a refractive index detector as a concentration detector can accurately determine the average molecular weight for any point in the chromatogram and analysis of the entire chromatographic distribution can be used to determine the weight-average molecular weight (Mw) when the value of dn/dc is obtained.

In the Rayleigh-Gans-Debye equation (Equation (1)), the light scattering signal in proportional to average molecular weight and sample concentration at any point in the chromatogram and specific increment of refractive index (dn/dc).

$$R(\theta) = K^* MCP(\theta)[1 - 2A_2 MCP(\theta)] \tag{1}$$

In Equation (1), $R(\theta)$ is the excess (from the solute alone) Rayleigh ratio (i.e. the ratio of the scatter and incident light intensity, corrected for size of scattering volume and distance from scattering volume), M is molar mass (molecular weight), C is analyte concentration, $K^*$ is the Rayleigh ratio constant, determined according to Equation (2)

$$K^* = (4\pi^2(n_o)^2/N_A(\lambda_o)^4)(dn/dc) \tag{2}$$

In Equation (2), $n_o$ is the solvent refractive index, $N_A$ is the Avogadro number, $\lambda_o$ is the vacuum wavelength of incident light, dn/dc is the specific refractive index increment, $P(\theta)$ is the form factor or scattering function and relates the angular variation in scattering intensity to the mean square radius ($r_g$) of the particle, $A_2$ is a second viral coefficient, a measure of solute solvent interaction.

From this analysis, number average molecular weight (Mn), weight-average molecular weight (Mw), polydispersity (Mw/Mn), and peak molecular weight (Mp) can be determined.

Instrumentation:

SEC/MALS/RI system was composed of Shimadzu LC 20A system, Wyatt Optilab rEX RI detector and Wyatt DAWN HELEOS-II MALS detector.

Molecular weight (Mw and Mn) and polydispersity (Mw/Mn) were calculated using Astra (Version: 5.3.4.20) software from Wyatt.

Tosoh TSKgel G3000PWxL (7 μm, 7.8 mm I.D×30 cm) with pre-column Tosoh TSKgel G6000PWxL (13 μm, 7.8 mm I.D×30 cm) were used for SEC analysis of the polymers.

Analytical Conditions:
Mobile phase: 0.45 M sodium nitrate aq.+0.5% (v/v) trifluoroacetic acid (TFA),
Flow rate: 0.5 ml/min
Detection:
Wavelength of linearly polarized laser in MALS: 658 nm
RI
Temperature: 25° C.
Injection volume: 50 μL
Sample dilution: 10 mg of the polymer (at concentration as indicated in Table 2) diluted by 1.5 mL mobile phase
Run time: 58 min Porous Support:
B1 Silica Gel Davisil LC 250, 40-63 μm (supplied by W. R. Grace)
B2 Silica Gel XWP500A, 35-75 μm (supplied by W. R. Grace)
B3 Silica Gel XWP1000A, 35-75 μm (supplied by W. R. Grace)

The properties of the porous supports B1 to B3 are given in Table 3 below.

TABLE 3

Properties of the porous supports

| Porous support | Pore size | Particle size distribution |
|---|---|---|
| B1 | 250 Å | 40-63 μm |
| B2 | 500 Å | 35-75 μm |
| B3 | 1,000 Å | 35-75 μm |

The pore size of the porous support was determined by mercury intrusion according to DIN 66133.

The particle size distribution of the porous support was determined by Malvern Laser Diffraction.

Cross-Linker
1,6-hexanediol diglycidylether (HDGE; ipox RD18 supplied by Ipox Chemicals)
1,4-butanediol diglycidylether (BDGE; supplied by Sigma-Aldrich and ipox RD3 supplied by Ipox Chemicals)

Example 1

Step 1

A 15 ml aqueous solution of polymer A2 (11% of polymer A2 in the solution) was mixed with a solution (704 μl) of 1,6-hexanediol diglycidylether (HDGE) to reach 7-9% of the cross-linker. The cross-linker ratio was calculated considering the amount of reacting groups versus the vinylamine units present in the polymer solution used for the reaction. After mixing, the pH was adjusted to 11 with 0.5 M NaOH.

10 g of porous support B1, dry powder, were sedimented into a flat bottom stainless steel dish with 8 cm diameter. 39.5 g of the polymer-cross-linker solution were added dropwise and equally distributed over the porous support and mixed using a spatula. The resultant paste was shaken for 1 min on a gyratory shaker at 600 rpm, in order to obtain a homogeneous mass with smooth surface. After covering the dish with a stainless steel lid, the paste was heated without further mixing or moving for 24 hours in an oven at 60° C. yielding a moist composite.

Step 2

1.3 ml of 0.5 M NaOH was added to 6.3 g of an aqueous solution of polymer A5 (7% of polymer A5 in the solution). After mixing, 17 ml of water were added into the solution, constituting the polymer A5 solution to be used for the next steps of the synthesis.

An aliquot of 29 g of the moist composite prepared in step 1 was washed on a frit with four times 25 ml of water. Then, this composite cake was suspended into 22 ml of the polymer A5 solution in an Erlenmeyer flask and shaken for 24 hours at 60° C.

Subsequently, the wet paste was washed on a frit with three times 25 ml of water. Then, the composite cake was suspended in 20 ml of 10% sulphuric acid and treated in a shaker bath for two hours at ambient temperature (23° C.) in order to quench (hydrolyse) unreacted epoxy groups. Finally, the product was washed on a frit with once more six times 25 ml of water and then stored in 20% ethanol-water.

Examples 2 to 10

Examples 2 to 10 were prepared in the same way as Example 1 but using the starting materials and cross-linker ratios listed in Table 4.

The amount of polymer for step 1 was adjusted taking into account the pore size and surface area of the porous support, considering the fact that not all silicas have the same pore volume to be filled. The amount of the second polymer added to the moist composite for step 2 was kept constant (ratio polymer to silica weight) for the examples presented here.

TABLE 4

| | First cross-linked polymer | Second non-cross-linked polymer | Porous support | Cross-linker ratio | Cross-linker | Moist composite for step 2 (g) |
|---|---|---|---|---|---|---|
| Example 1 | A2 | A5 | B1 | 7-9% | HDGE | 29.0 |
| Example 2 | A2 | A5 | B2 | 7-9% | BDGE | 11 |
| Example 3 | A2 | A5 | B3 | 7-9% | BDGE | 11 |
| Example 4 | A1 | A3 | B2 | 7-9% | BDGE | 14.5 |
| Example 5 | A3 | A3 | B2 | 12% | BDGE | 14.6 |
| Example 6 | A1 | A6 | B2 | 7-9% | BDGE | 37.2 |
| Example 7 | A1 | A9 | B2 | 7-9% | BDGE | 12 |
| Example 8 | A1 | A10 | B2 | 7-9% | BDGE | 12 |
| Example 9 | A7 | A1 | B2 | 7-9% | BDGE | 17 |
| Example 10 | A8 | A1 | B2 | 7-9% | BDGE | 15 |

In order to demonstrate the advantages of covalently bonding a second polymer on the outer surface of a composite formed of a crosslinked polymer-filled porous support, composites composed of a porous support filled with a cross-linked polymer were prepared as detailed below.

Comparative Example 1

15 ml of aqueous solution of polymer A1 (15% of polymer A1 in the solution) was mixed with a solution (704 μl) of 1,6-hexanediol diglycidylether (HDGE) to reach 7-9% of the cross-linker. The cross-linker ratio was calculated considering the amount of reacting groups versus the vinylamine units (monomers) present in the polymer solution used for the reaction. After mixing, the pH was adjusted to 11 with 0.5 M NaOH.

10 g of the dry powder porous support B1 were sedimented in a flat bottom stainless steel dish with 8 cm diameter. The porous support B1 was impregnated with 39.5 g of the polymer-cross-linker solution which was added dropwise and equally distributed over the porous support and mixed using a spatula. The resultant paste was shaken for 1 min on a gyratory shaker at 600 rpm, in order to obtain a homogeneous mass with smooth surface. After covering the dish with a stainless steel lid, the paste was heated without further mixing or moving for 48 hours in an oven at 60° C. yielding 49.6 g of moist composite.

Subsequently 41.3 g of this moist composite was washed on a frit with five times 25 ml of water. Then, the composite cake was suspended in 31.6 ml of 10% sulphuric acid and treated in a shaker bath for two hours at ambient temperature (23° C.) in order to hydrolyse unreacted epoxy groups. Finally, the product was washed on a frit with once more five times 25 ml of water and then stored in 20% ethanol-water.

Comparative Examples 2 to 7

Comparative Examples 2 to 7 were prepared in the same way as Comparative Example 1 but using the starting materials listed in Table 5.

TABLE 5

| | Polymer | Porous support | Cross-linker ratio | Cross-linker |
|---|---|---|---|---|
| Comp. Example 1 | A1 | B1 | 7-9% | HDGE |
| Comp. Example 2 | A2 | B1 | 7-9% | HDGE |
| Comp. Example 3 | A2 | B2 | 7-9% | BDGE |
| Comp. Example 4 | A2 | B3 | 7-9% | EDGE |
| Comp. Example 5 | A1 | B2 | 7-9% | BDGE |
| Comp. Example 6 | A7 | B2 | 7-9% | BDGE |
| Comp. Example 7 | A8 | B2 | 7-9% | BDGE |

Determination of the Depletion Performance and hIgG Recovery of the Composite Materials of the Examples In order to measure the purification capability of the composite materials, the degree of depletion (separation) of impurities or undesired compounds from the target substance is determined. For this purpose the concentration of individual components in the feed is determined using selective assays. After the purification step, this concentration measurement is repeated with the purified fraction. Thus, it is possible to calculate both purity and recovery from these concentrations and the related volumes.

Feed

The feed was an untreated and undiluted Cell Culture Supernatant CHO-K1 spiked at 2 mg/ml of hIgG from human blood plasma (Octagam, 10% solution, Octapharma, Vienna).

Cell Culture Supernatants (CCSs)
CCS1
  CHO-K1, Invivo, Berlin
  Cell Line CHO-K1 ($2.5 \times 10^6$ viable cells/ml)
  Conductivity: 15 mS/cm
  Average Host Cell Protein (HCP) concentration 100-150 µg/ml
  Average DNA concentration between 700-1,000 ng/ml
CCS2
  CHO-K1, Invivo, Berlin
  Cell Line CHO-K1
  Conductivity: 13 mS/cm
  Average Host Cell Protein (HCP) concentration 65-82 µg/ml
  Average DNA concentration between 250-500 ng/ml
CCS3
  CHO-K1, Invivo, Berlin
  Cell Line CHO-K1
  Conductivity: 13 mS/cm
  Average Host Cell Protein (HCP) concentration 150-200 µg/ml
  Average DNA concentration between 500-1,100 ng/ml All adsorbents were equilibrated with 50 mM ammonium acetate at pH 6.5 prior to contacting with the feed.

20 mg of the adsorbent were incubated with 1 ml of the feed using an Eppendorf or a centrifugation tube. The ratio of feed volume to adsorbent weight was 50:1 (1 ml feed:0.02 g adsorbent). After 5 min of gentle shaking, the supernatant was separated by centrifugation for subsequent analysis. Unless otherwise specified, contact time is 5 min.

To determine the efficiency of depletion of host cell proteins (HCPs) and DNA, as well as the hIgG recovery, the quantification of the above three substances was performed in the raw feed and the depleted feed, after a specified contact time with the composite material. Both values were subsequently compared.

Host Cell Protein (HCP) Determination

Cygnus CHO HCP Elisa Kit 3G was used to determine the efficiency of depletion of host cell proteins (HCPs), CHO Host Cell Proteins $3^{rd}$ Generation (#F550), from Cygnus Technologies, Southport (USA) according to the manufacturer's instructions (manual "800-F550, Rev. 3, 21JUL2015"), on a VictorX Spectrophotometer and corresponding software from PerkinElmer (Courtaboeuf, France) for reading and data evaluation. Samples were diluted in the sample diluent (Product catalog number #I028 purchased from Cygnus Technologies).

The HCP depletion is expressed as:

$$\text{HCP depletion (\%)} = 100 \times (\text{HCP concentration in supernatant})/(\text{HCP concentration in initial spiked CCS})$$

In the above formula, "supernatant" refers to the purified CCS.

DNA Determination

The samples to be analysed were the starting CCSs (with or without hIgG spiked) and the depleted samples.

The DNA quantification was accomplished utilizing DNA-specific fluorescence assay using Quant-iT™ PicoGreen® dsDNA Reagent Kit (#P7589), Invitrogen (Germany) after DNA extraction with the DNA Extraction Kit (#D100T), Cygnus Technologies, Southport (USA), according to the manufacturer's instructions, on a VictorX Spectrophotometer and corresponding software from PerkinElmer (Courtaboeuf, France) for reading and data evaluation.

The DNA depletion is expressed as:

$$\text{DNA depletion (\%)} = 100 \times (\text{DNA concentration in supernatant})/(\text{DNA concentration in initial spiked CCS})$$

In the above formula, "supernatant" refers to the purified CCS.

hIgG Recovery Determination by Size Exclusion Chromatography (SEC)

The recovery of hIgG was determined by quantitative SEC as follows.

The concentration of hIgG in the feed and the recovery rate of hIgG in the purified solution have been determined with SEC under the following conditions.
  Column: TSKgel UP-SW3000 4.6×300 mm (particle size 2 µm) from Tosoh Bioscience LCC.

Mobile Phase: 100 mM sodium phosphate pH 6.7 buffer+ 100 mM Na$_2$SO$_4$+0.05% NaN$_3$ Injection volume: 10 μL—sample diluted with the mobile phase.

Flow rate: 0.35 ml/min.

Detector: DAD 280 nm.

Temperature: 25° C.

This column with high efficiency and the associated analytical conditions allow appropriate quantification of the monomer and dimer peaks.

The hIgG recovery is expressed as:

Recovery (%)=100×(hIgG concentration in supernatant)/(hIgG concentration in initial spiked CCS)

In the above formula, "supernatant" refers to the purified CCS.

The results are shown in Table 6.

TABLE 6

Depletion performance of the composites of the examples at 50:1 feed:composite ratio

| | HCP depletion (%) | DNA depletion (%) |
|---|---|---|
| Example 1 | 63 | 82 |
| Example 2 | 73 | 91 |
| Example 3 | 71 | 90 |
| Example 4 | 71 | 85 |
| Example 5 | 68 | 78 |
| Example 6 | 67 | 75 |
| Example 7 | 78 | 83 |
| Example 8 | 62 | 93 |
| Example 9 | 83 | 97 |
| Example 10 | 70 | 85 |
| Comp. Example 2 | 63 | 89 |
| Comp. Example 3 | 37 | 78 |
| Comp. Example 4 | 48 | 84 |
| Comp. Example 5 | 49 | 59 |
| Comp. Example 6 | 9 | 15 |
| Comp. Example 7 | 15 | 74 |

The recovery rates of hIgG at 50:1 feed:composite ratio of Examples 1 to 8 and 10 were nearly quantitative (≥96%). The recovery rate of Example 9 was slightly lower at 90%.

The above measurements were repeated for Examples 1 to 6 using a 5:1 feed:composite ratio.

The composites of Examples 1 to 6 depleted DNA and HCPs from the feedstocks at >95% when 5:1 feedstock: composite ratio was used.

Without wishing to be bound to any theory, it is believed that the hIgG remains mostly excluded from the particles and smaller proteins (HCPs) and DNA get adsorbed in or around the particles.

As seen in Table 6, Example 1 and Comparative Example 2 have similar depletion performance. On the other hand, Example 2 (comprising a porous support having an average pore size of 500 Å) has significantly superior performance than Comparative Example 3 (comprising a porous support having an average pore size of 500 Å but not comprising a second polymer). Similarly, Examples 4 and 6 to 8 have significantly superior performance than Comparative Example 5 (not comprising a second polymer), and Examples 9 and 10 are significantly superior to Comparative Examples 6 and 7, respectively. Examples 2, 3, 7 and 9, wherein the second polymer has a higher weight average molecular weight (Mw) than the first polymer have especially high DNA and HCP depletion capabilities.

The invention claimed is:

1. A composite material comprising:
   a porous support having an average pore size of 5 to 500 nm, said porous support being filled with a first polymer which is cross-linked, and
   a second polymer which is not cross-linked and is covalently bonded to the external surface of the cross-linked polymer-filled porous support,
   wherein the first polymer contains functional groups of hydroxyl, thiol, carboxyl, sulfonyl, amino, or combinations thereof,
   wherein the second polymer contains functional groups of hydroxyl, thiol, carboxyl, sulfonyl, amino, or combiations thereof,
   wherein the first polymer is polyvinylamines or polyallylamines, the first polymer being cross-linked with butanediol diglycidylether (BDGE) or hexanediol diglycidylether (HDGE) and
   wherein the second polymer is polyvinylamines or polyallylamines.

2. The composite material according to claim 1, wherein the polyvinylamine is a linear or branched homopolymer of vinylamine or a copolymer of vinylamine and vinylformamide.

3. The composite material according to claim 1, wherein said polyvinylamine or polyallylamine has a hydrolysis degree of the formamide groups of at least 50%.

4. The composite material according to claim 1, wherein the porous support is a particulate material with an average particle size of 1 to 500 μm.

5. The composite material according to claim 1, wherein the weight average molecular weight (Mw) of the second polymer is higher than the weight average molecular weight (Mw) of the first polymer.

6. A method for purifying a target protein in a feedstock, said method comprising the steps of:
   i) contacting the feedstock with a composite material according to claim 1 for a sufficient time;
   ii) separating the composite material from the purified feedstock;
   iii) optionally, isolating the purified target protein from the feedstock; and
   iv) optionally, washing the composite material with a solvent and collecting the obtained solution for further processing.

7. The method according to claim 6, wherein the target protein is a monoclonal antibody.

8. The method according to claim 6, wherein the contact time is at least 1 min.

9. The composite material according to claim 2, wherein said polyvinylamine or polyallylamine has a hydrolysis degree of the formamide groups of at least 50%.

* * * * *